United States Patent [19]

Kloczko et al.

[11] Patent Number: 6,063,392
[45] Date of Patent: May 16, 2000

[54] METHOD OF APPLYING AN ACTIVE SUBSTANCE TO PLANTS AND A SUITABLE PREPARATION

[75] Inventors: Malgorzata Kloczko, Linz; Michael Roreger, Neuwied, both of Germany

[73] Assignee: LTS Lohmann Therapie-System GmbH, Neuwied, Germany

[21] Appl. No.: 09/101,904

[22] PCT Filed: Dec. 23, 1996

[86] PCT No.: PCT/EP96/05823

§ 371 Date: Jul. 15, 1998

§ 102(e) Date: Jul. 15, 1998

[87] PCT Pub. No.: WO97/25863

PCT Pub. Date: Jul. 24, 1997

[30] Foreign Application Priority Data

Jan. 17, 1996 [DE] Germany ............................ 196 01 430

[51] Int. Cl.[7] .......................... A01N 25/24; A01N 25/00; A01G 17/18; A01G 17/12
[52] U.S. Cl. ........................ 424/407; 424/405; 424/195.1; 47/24; 47/DIG. 1; 47/8
[58] Field of Search ..................................... 424/405, 407, 424/195.1; 504/116; 71/DIG. 1; 47/8, 24, DIG. 1

[56] References Cited

U.S. PATENT DOCUMENTS

| 3,756,801 | 9/1973 | Herschler ..................................... 71/65 |
| 4,456,587 | 6/1984 | Keith . |
| 5,395,851 | 3/1995 | Sedun ........................................ 514/494 |

FOREIGN PATENT DOCUMENTS

| 272219 | 10/1989 | German Dem. Rep. ...... A01N 25/02 |
| 3507008 | 8/1986 | Germany . |
| 273573 | 11/1989 | Germany ........................ A01N 57/12 |
| 4430449 | 2/1996 | Germany ........................ A01N 25/24 |

*Primary Examiner*—Thurman K. Page
*Assistant Examiner*—Todd D. Ware
*Attorney, Agent, or Firm*—Ann W. Speckman; James E. Klaniecki

[57] ABSTRACT

A method of applying a layer-form active ingredient depot with delayed release of active ingredients to plants or plant parts, having at least one pressure-sensitively adhering matrix layer (A) which comprises active ingredient and is in two-dimensional contact with the plant surface, and one back layer (B) which is essentially free from and impermeable to active ingredient and is on the side remote from the plant is characterized in that the layer (A) is produced by painting in the desired two-dimensional pattern at the site of application on the plant from a spreadable, pressure-sensitively adhering, polymer-based composition which comprises active ingredient and then on the said layer (A) the layer (B) is produced by painting or spraying.

18 Claims, No Drawings

METHOD OF APPLYING AN ACTIVE SUBSTANCE TO PLANTS AND A SUITABLE PREPARATION

TECHNICAL FIELD OF THE INVENTION

The invention relates to a method of applying a layer-form active ingredient depot with delayed release of active ingredients to plants or plant parts, having at least one pressure-sensitively adhering matrix layer (A) which comprises active ingredient and is in two-dimensional contact with the plant surface, and one back layer (B) which is essentially free from and impermeable to active ingredients and is on the side remote from the plant; the invention embraces a two-component or multicomponents preparation suitable for this method.

BACKGROUND OF THE INVENTION

For treating the wounds of cut surfaces on plants, especially trees, which come about as a result of cutting back or pollarding, pruning or thinning of budding or grafting, use has long been made of filler-comprising covering compositions which initially were formed essentially by natural materials, such as tar or tree wax, or—borrowed from the building sector—were based on mortarlike or paintlike compositions.

With the increasing development of synthetic resins, laminates and polymers, and also of active ingredients and pesticides, especially fungicides, more differentiated methods of plant treatment were developed.

For instance, as early as in DE-C 1 281 206, a composition for treating tissue-damaged plants was described which comprises an aqueous synthetic-resin dispersion which has cellulose as its filler, is intended for brush application and binds well to the plant.

DE-A 2 023 262 discloses a pesticidal pest control composition for forestry which is applied in mobile form and hardens in air to become viscous.

U.S. Pat. No. 4,456,587 provides a mixture which is intended for spray application to the leaves of the plants that are to be treated and which is based on polyvinyl alcohol/polyvinyl pyrrolidone in aqueous dispersion, in which an active ingredient (pheromone or insecticide), mixed with oil, is finely divided. The polymer mixture dries or "cures" on the plant and releases the active ingredient to the plant over a period of several weeks.

DE-A 35 07 008 emphasizes the positive effect of finely ground rock flour ($<4\mu$) in a spreadable plant treatment composition based on polymers, synthetic resins or natural resins.

DD 272 219 describes treating tree wounds by brushing them with two coats of paint, which involves first of all coating the bark of the tree with a latex binder and, after it has set, carrying out treatment with a composition which comprises active ingredient, alkyd resin and phyllosilicate.

DD 273 573 A1 reveals a pastelike composition for controlling bark-breeding pests, such as bark beetles, which is spread onto the bark and which in addition to the active ingredient(s) comprises terpene hydrocarbons, such as α-pinene, or myrcene, and is suitable for the controlled, delayed release of active ingredient(s). Covering with plastic film is recommended as a means of avoiding environmental contamination.

Again, more recently, DE Patent Application P 44 30 449.8 has proposed a sprayable preparation of active ingredient which results in a water-insoluble, pressure-sensitively adhering film with controlled, delayed release of active ingredient.

U.S. Pat. No. 5,395,851, finally, describes a sprayable or spreadable composition comprising a fungicide in a mixture of natural and synthetic resin and metal salts of fatty acids.

None of these diverse efforts appears to be entirely satisfactory: the coverings produced in feasible technology, with more or less good adhesiveness, have the disadvantage that there may be losses of active ingredient into the surroundings, especially as a result of the effects of weathering, and that there is an increased risk to free-living animals. Layer application by spray technology is not without its problems for the user, and layers having good adhesiveness can result in adjacent plant parts becoming stuck.

An additional covering with plastic film is to start with complex and ackward and, moreover, is not always possible when there are spatial constraints.

SUMMARY OF THE INVENTION

The present invention is therefore based on the object of providing, for the administration of active ingredients to plants, systems which externally release active ingredients over a prolonged period without notable losses with the aim of a sustained therapeutic effect. These systems should be readily handleable with no hazard to the user and should be able to be applied with no spatial restriction (in other words, for example, to ground cover plants as well).

The achievement of this object is obtained in a surprisingly simple manner by the method according to the characterizing features of the main claim and with a corresponding active ingredient depot preparation which complies fully with the abovementioned requirements. Further embodiments, essential to the invention, of the active ingredient preparation are provided in accordance with the subclaims.

"Self-adhesive" or "pressure-sensitively adhering" means here "of permanent surface tackiness, both before and after application".

Although DE-C 39 22 366 has already disclosed ready-to-use active ingredient depot systems in the form of so-called plasters, which have an analogous layering and functionality at the site of application, such systems are complex and their use is limited for reasons of space.

In accordance with the invention, application results in a layer structure comprising an outer layer which is essentially impermeable to active ingredients and to water, and one or more pressure-sensitively adhering matrix layers which face the plant and comprise active ingredient. The simple mode of application makes it possible to treat plants of different morphologies without restriction. Essential to the invention is the presence of an inert, non-adhering back layer, which protects the active-ingredient-comprising matrix against the effects of weathering in that it entirely covers this matrix. In this way, the danger of environmental contamination and the danger of the unwanted sticking of other plant parts are avoided.

DETAILED DESCRIPTION

The systems presented below are applied by the painting method using brushes and applicator sponges. The individual layers are applied separately—that is, in terms of time—atop one another. The compositions to be used for this purpose can be supplied from containers or dispensers featuring a dual-chamber of multichamber system. In this arrangement the individual components are disposed such that the component which comprises active ingredient and has a pressure-sensitively adhering composition is coated first of all onto the plant surface in the form of a single-coat or multicoat covering. Not until the component has slightly dried is it covered over the whole of its area with the second layer, which is free from active ingredient.

The top layer here can also be produced by spraying (or foaming).

For this purpose the preparation to be sprayed is dispensed into a pump can which is free from propellant gas and has a press-down atomizer. In cases such as these the active-ingredient-free preparation will of course have a relatively low viscosity so as to ensure flawless spraying.

Important constituents of preparations according to the invention are polymers, which possess both the function of an active ingredient carrier (matrix) and that of the raw materials for the back layer.

For the pressure-sensitively adhering matrix layer of the plaster according to the invention use is made of homo- or copolymers of esters of acrylic acid, such as ethyl acrylate and n-butyl acrylate, and also methacrylic methyl ester. Further suitable polymers are ethylene-vinyl acetate or triblock polymers such as styrene-butadiene-styrene. They are processed on the basis of a solution in organic solvents or of an aqueous dispersion, aqueous systems being preferred on account of their favourable ecological properties.

In the case of polymers which do not adhere pressure-sensitively, appropriate auxiliaries must be added in order to achieve desired properties. This function is served principally by resinous substances, such as modified natural resins, especially rosin and its derivatives, polyterpene resins, and hydrocarbon resins. Particularly suitable such substances which may be emphasized here are rosin esters (such as Foral® 85 and Staybelite Ester® 10). The amount of the resin additive depends on the desired properties and is subject to an upper limit, since with too great a proportion of resin the cohesion of the resulting coverings becomes too low. The said amount can vary between 1.0 and 20.0% by weight and is usually in the range from 5 to 10% by weight, based on the solids content of the preparation.

The relative proportions of active ingredient and polymer in the matrix can vary over a wide range depending on the desired effect. The proportions can be in the range from 1% active ingredient and 99% active ingredient and 1% polymer. Proportions giving good results include 1 part of active ingredient to 10–30 parts of polymer.

If required, the active ingredient matrix may comprise penetration accelerants and mixtures thereof, normally in concentrations from 1 to 10% by weight. Examples of penetration accelerants which can be employed are long-chain alcohols, 2-pyrrolidone derivatives, mono-, di- and triglycerides, fatty acids, fatty acid esters, and many others.

The active ingredients present in plasters according to the invention can be in solution or dispersion in the polymer matrix. They may be present individually or in a mixture.

A particularly advantageous embodiment of the systems according to the invention are those in which active ingredients are subject to (diffusion-)controlled release. A prerequisite for this, however, is that the active-ingredient-comprising component is applied with an applicator which makes it possible to regulate both the overall surface area and the thickness of the layer that is to be applied. In this context, the overall area of active ingredient release that is to be achieved may be composed of a plurality of unit areas, which are preferably applied dotwise. The applicator can be of various configuration, such as, for example, in the form of a flexible stencil. A further option is that of dispenser systems, such as, for example, injection dispensers or a screen printing plate, which may additionally be integrated into the release container.

Among the active ingredients which can be released to plants by means of the preparations according to the invention, mention should be made primarily of systemic plant protection agents (fungicides, insecticides, acaricides, bactericides) and also growth regulators.

Examples, of systemic fungicides are benomyl, bromuconazole, bitertanol, etaconazole, flusilazole, furalaxyl, fosetyl-aluminium, imazalil, metalaxyl, propiconazole, thiabendazole, triadimefon and triticonazole.

Examples of systemic insecticides are butocarboxim, dimethbate, imidacloprid, fenoxycarb, methamyl, oxamyl, pirimicarb and propoxur.

Examples of systemic acaricides are clofentezine, fenbutatin oxide and hexythiazox.

Examples of systemic growth regulators are ethephon and β-indolylacetic acid (IAA).

Among the systemic bactericides mention may be made, for example, of flumequine.

In accordance with the protective function of the cover layer, the starting materials used to produce it on the plant should possess a relatively high diffusion resistance and have hydrophobic properties. Substances suitable for this purpose include polyvinyl acetate, cellulose derivatives, chitosan and others. Cellulose derivatives such as cellulose acetate or cellulose butyrate are particularly advantageous because they are biodegradable.

All of the said polymers are applied as fluid or pasty media to the previously applied active ingredient layer. For this purpose they are generally mixed with appropriate solvents. Suitable solvents which can be used for this purpose are ethyl acetate, acetone, ethanol, isopropanol or mixtures thereof. The amount of the solvent or solvent mixture must be chosen so that the overall preparation has a viscosity which enables it to be applied by spreading. With this application technique, good results can be achieved with compositions whose viscosity lies between 1.5 and 3.0 Pa.s. The polymer content of such compositions is judiciously about 25–80% by weight, preferably from 50 to 65% by weight.

The active ingredient release systems according to the invention can be used to provide controlled administration of bioactive substances to plants. A preferred field of use for these systems is the plant protection sector. The examples which follow serve to illustrate the invention. All amounts, proportions and percentages are based, unless specified otherwise, on the overall weight of the respective preparation of components.

EXAMPLE 1

29 parts by weight of the fungicide triticonazole were dispersed together with 2 parts by weight of the insecticide imidacloprid (both active ingredients suspended in 5 parts by weight of 1-methyl-2-pyrrolidone) in 65 parts by weight of an aqueous, polyacrylate-based adhesive dispersion (Collano® AGX-23; solids content 61%), with continual stirring. The resulting, active-ingredient-comprising dispersion, whose relative viscosity at 24° C. was 1.52 Pa.s (according to Brookfield LVF/measuring body), was applied with the aid of a brush to the main shoots of an infested rose tree (0.25 g of composition per shoot) and was spread out to form a stripe about 1 cm in width and 5 cm long. This pressure-sensitively adhering layer, comprising active ingredient, was subsequently covered with an approximately 0.1 mm thick layer of a polyvinyl acetate solution (33% strength solution of polyvinyl acetate in ethyl acetate), which was likewise applied by the painting method.

EXAMPLE 2

6 parts by weight of ethylcellulose (Ethylcellulose NF®50) were dissolved with stirring in 25 parts by weight of a solvent mixture of ethyl acetate and ethanol (ethyl acetate:ethanol=1:4). Following the addition of 15.0 parts by weight of a resin (Hercolyn®D) as tackifier, 3.5 parts by weight of the active ingredient imidacloprid and 42.5 parts by weight of the active ingredient triticonazole were added to the resulting, pressure-sensitively adhering composition, the active ingredients being in suspension in 8 parts by weight of 1-methyl-2-pyrrolidone. The added active ingredients were distributed uniformly in the composition with continual stirring. The resulting highly viscous (pasty), pressure-sensitively adhering composition comprising active ingredients was spread using a brush onto the main shoots of a rose tree (in the base region) (0.35 g of composition per shoot). A film of cellulose acetate butyrate was produced on the active-ingredient-comprising layer by spreading on 0.1 g of a 25% strength solution of cellulose acetate butyrate in acetone.

What is claimed is:

1. A dispenser for applying compositions to plant surfaces for treating plants with at least one controllably releasable plant-active ingredient, comprising a first reservoir containing a spreadable, adhesive matrix composition comprising the at least one plant-active ingredient, and a second reservoir containing a spreadable or sprayable composition for application to an exposed surface of the adhesive matrix composition, thereby providing a backing layer covering the exposed surface of the adhesive matrix composition that is essentially free from and impermeable to the at least one plant-active ingredient and being in a spreadable or a sprayable form.

2. A method of treating plant surfaces with at least one plant-active ingredient that is controllably releasable from an adhesive matrix layer covered by a backing layer, characterized in that the adhesive matrix layer comprising at least one plant active ingredient is applied to a plant surface to be treated using a spreadable, matrix layer-forming composition, and the exposed surface of the matrix layer is covered with the backing layer, the backing layer being essentially free from and impermeable to the at least one plant-active ingredient and being in a spreadable or a sprayable form.

3. A dispenser according to claim 1, characterized in that the first reservoir contains a spreadable solution in an organic solvent or a spreadable aqueous dispersion of a homo- or copolymer or of polymer mixtures with auxiliaries and additives and with active ingredients dispersed therein.

4. A dispenser according to claim 1, characterized in that the first reservoir contains, in amounts of from 1 to 20% by weight based on the solids content of the first reservoir, resinous substances which promote the adhesive properties.

5. A dispenser according to claim 1, characterized in that the first reservoir contains about 1 part of one or more active ingredients to from 10 to 30 parts of polymer.

6. A dispenser according to claim 1, characterized in that the first reservoir contains penetration accelerants.

7. A dispenser according to claim 1, characterized in that the spreadable solution in the first reservoir is suitable for producing a matrix layer providing controllable release of active ingredient.

8. A dispenser according to claim 1, characterized in that the first reservoir contains, as systemic active ingredients, plant protection agents, plant strengthening agents, growth regulators, nutrients and/or agents for regulating biological processes.

9. A dispenser according to claim 1, characterized in that the second reservoir contains a spreadable or sprayable composition suitable for forming a lipophilic top layer which is inert to active ingredients and has high diffusion resistance.

10. A dispenser according to claim 1, characterized in that the second reservoir contains a solution of cellulose acetate or cellulose butyrate having a polymer content of 25–80% by weight, and a viscosity of 1.5–3 Pa.s.

11. A multicomponent preparation for application to a plant, comprising: a first adhesive matrix layer comprising at least one plant-active ingredient; and a backing layer for covering an exposed surface of the first adhesive matrix layer, the backing layer being essentially free from and impermeable to the at least one plant-active ingredient and being in a spreadable or a sprayable form.

12. A preparation according to claim 11, wherein the first adhesive matrix layer is formed from a spreadable solution in an organic solvent or a spreadable aqueous dispersion of a homo- or copolymer, or of polymer mixtures with auxiliaries and additives and with active ingredient dispersed therein.

13. A preparation according to claim 11, wherein the first adhesive matrix layer comprises, in an amount of from 1% to 20% by weight, based on solids content, resinous substances that impart adhesive properties.

14. A preparation according to claim 11, wherein the first adhesive matrix layer comprises about 1 part of one or more active ingredients to from 10 to 30 parts of polymer.

15. A preparation according to claim 11, wherein the first adhesive matrix layer comprises penetration accelerants.

16. A preparation according to claim 11, wherein the first adhesive matrix layer comprises a plant protection agent, a plant stregthening agent, a plant growth regulator, a plant nutrient, and/or an agent for regulating biological processes.

17. A preparation according to claim 11, wherein the backing layer is lipophilic and has a high diffusion resistance.

18. A preparation according to claim 11, wherein the backing layer comprises cellulose acetate or cellulose butyrate having a polymer content of 25%–80%, by weight, and a viscosity of 1.5–3 Pa.s.

* * * * *